US009072566B2

(12) United States Patent
König

(10) Patent No.: US 9,072,566 B2
(45) Date of Patent: Jul. 7, 2015

(54) DENTAL IMPLANT

(75) Inventor: Arno König, Zurich (CH)

(73) Assignee: Dentalpoint AG, Zurich (CH)

( * ) Notice: Subject to any disclaimer, the term of this patent is extended or adjusted under 35 U.S.C. 154(b) by 30 days.

(21) Appl. No.: 12/669,459

(22) PCT Filed: Jul. 16, 2007

(86) PCT No.: PCT/CH2007/000342
§ 371 (c)(1),
(2), (4) Date: Apr. 6, 2010

(87) PCT Pub. No.: WO2009/009910
PCT Pub. Date: Jan. 22, 2009

(65) Prior Publication Data
US 2010/0196851 A1  Aug. 5, 2010

(51) Int. Cl.
*A61C 8/00* (2006.01)
(52) U.S. Cl.
CPC .............. *A61C 8/005* (2013.01); *A61C 8/0066* (2013.01)
(58) Field of Classification Search
CPC .. A61C 8/0001; A61C 8/0012; A61C 8/0018; A61C 8/0019; A61C 8/0022; A61C 8/0048; A61C 8/005; A61C 8/0054; A61C 8/0057; A61C 8/006; A61C 8/0066; A61C 8/0069; A61C 8/0075; A61C 8/0078; A61C 8/0086
USPC ......... 433/173, 174, 221, 169, 172, 175, 176, 433/201.1
See application file for complete search history.

(56) References Cited

U.S. PATENT DOCUMENTS

| 4,468,200 | A |   | 8/1984  | Munch |         |
|-----------|---|---|---------|-------|---------|
| 4,645,453 | A | * | 2/1987  | Niznick | ........................ 433/173 |
| 5,030,095 | A |   | 7/1991  | Niznick |         |
| 5,104,321 | A | * | 4/1992  | Filhol | ............................ 433/221 |
| 5,263,996 | A | * | 11/1993 | Filhol | ............................ 433/221 |
| 5,897,320 | A | * | 4/1999  | Gittleman | ...................... 433/180 |
| 6,974,322 | B2 |   | 12/2005 | May et al. |     |
| 7,108,510 | B2 |   | 9/2006  | Niznick |         |
| 2004/0121285 | A1 |   | 6/2004 | Wu |          |
| 2005/0136378 | A1 | * | 6/2005 | Ennajimi et al. | .............. 433/173 |
| 2006/0127849 | A1 | * | 6/2006 | Levisman | ..................... 433/173 |
| 2006/0246399 | A1 | * | 11/2006 | Ehrl | .......................... 433/201.1 |

FOREIGN PATENT DOCUMENTS

DE   42 36 978 A1   5/1994
DE   10 2005 013 200 A1   9/2006
(Continued)

*Primary Examiner* — Cris L Rodriguez
*Assistant Examiner* — Justin O'Donnell
(74) *Attorney, Agent, or Firm* — Janet Sleath; Speckman Law Group PLLC

(57) ABSTRACT

A tooth replacement system is provided that includes an implant (10, 20, 30), for osseointegration in a jaw bone, and an abutment (40, 50, 60), wherein an abutment stem (41) including a close-fit cylinder (42) can be fitted in a corresponding cylindrical close-fit seat (14) of a receiving opening (11) in the implant. The present invention makes available a tooth replacement system including an implant and an abutment, which ensures an optimized introduction of force from the abutment into the implant and permits complete freedom in terms of the choice of material. The implant and also the abutment can be made from titanium or ceramic, and both structural parts can be used in all possible material combinations. This permits the insertion or adhesive bonding of ceramic abutments into implants made from titanium oxide or other metallic materials.

21 Claims, 5 Drawing Sheets

(56) References Cited

FOREIGN PATENT DOCUMENTS

| EP | 1452149 A1 * | 9/2004 | ............... A61C 8/00 |
| JP | 59-97658 | 6/1984 | |
| JP | 2011-505749 A | 5/1999 | |
| JP | 2001-104343 A | 4/2001 | |
| WO | 2007039206 A1 | 4/2007 | |

* cited by examiner

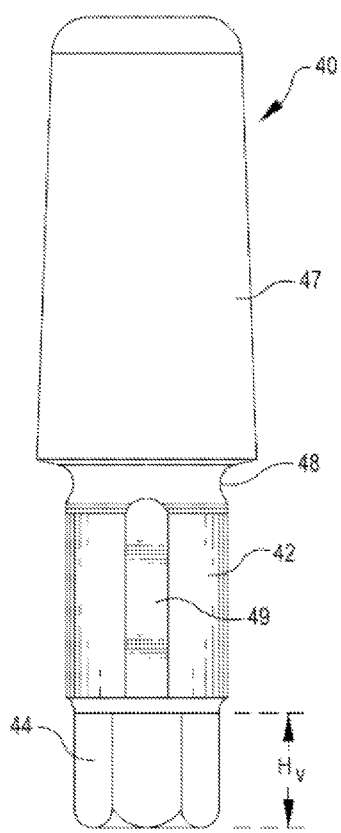
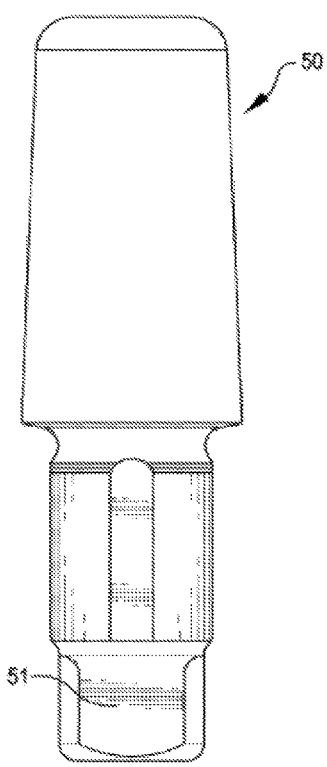
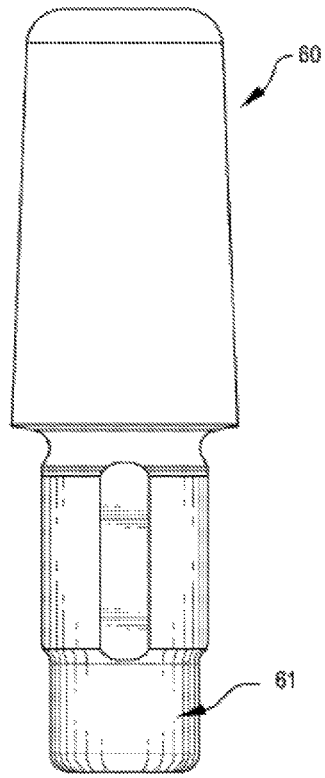

DENTAL IMPLANT

REFERENCE TO RELATED APPLICATIONS

This application is the US national phase entry of International Patent Application No. PCT/CH2007/000342, filed Jul. 16, 2007

FIELD OF THE INVENTION

The present invention relates to a tooth replacement system comprising an implant for osseointegration in a jaw bone and an abutment.

BACKGROUND OF THE INVENTION

For many years, a wide variety of tooth replacement systems have been offered on the market under the terms tooth implant or dental implant, and some of them have been used with great success. The terms tooth implant or dental implant generally stand for the tooth replacement per se and should not be confused with the actual implant body which, as tooth root replacement, is correctly designated as implant. In the text that follows, the terms tooth implant and implant body or implant are clearly distinguished, with the tooth implant designating the tooth replacement, which comprises the implant body for anchoring in the jaw bone. Two-part and three-part tooth implants predominate on the market, and the three-part tooth implants for replacement of an individual tooth generally consist of an endosseous implant or implant body, an abutment (also called connection part or implant post), and a crown, a bridge or another prosthesis. The abutment allows the dentist to orient the crown in relation to the implant, such that the exact position of the crown in the dental arch is not solely dependent on the setting of the implant body. The setting and the position of the implant is often determined by the particular anatomical situation in the patient's jaw. The setting of the crown can be corrected by means of suitably shaped or adjustable abutments or by working the abutment after insertion.

The choice of materials for the implant is greatly limited by stringent requirements in respect of biocompatibility and of the mechanical properties of the implant. In the last few decades, titanium in particular has become the preferred material, because it has a modulus of elasticity similar to the jaw bone and has excellent biocompatibility.

However, a disadvantage of the implants and abutments made of titanium lies in their dark colour. In the event of the gum and bone receding, the dark metal parts may become visible or show through especially in the area of the front teeth, which is extremely undesirable for cosmetic reasons. In recent years, therefore, ceramics, e.g. zirconium oxide ceramic, have attracted increasing interest as an alternative material.

Critics argue that the high modulus of elasticity of implants made from zirconium oxide ceramic leads to deep-seated fractures of the implant bodies and that their lesser degree of osseointegration compared to titanium may lead to extensive inflammation that breaks up the bone. Tooth implants made from titanium are in turn thought to trigger negative reactions through metal intoxication.

Customary implant shapes include blade, needle, screw, cylinder and cone implants, which are each used for different indications. These indications are defined by the amount of available bone, the quality of the bone and the functional goal. In principle, it is possible to use subperiosteal and endosseous implants, although in practice it is almost exclusively endosseous implants that are used at present, of the types with blade systems, screw systems or cylinder systems. Commonly used endosseous implants have a substantially cylindrical structure and are screwed or hammered into a bore in the jaw bone or directly into the jaw bone. At the coronal end, the implants are provided with an open blind bore for receiving the abutment. Since the abutment for receiving the crown or a bridge protrudes through the gum into the oral cavity and is not fully enclosed by the gum, such tooth implants are referred to as semi-open. In the semi-open implants, the crown, which is in most cases made from conventional dental ceramic and/or metal, is adhesively bonded or cemented onto the abutment or the one-piece implant/abutment structure or is secured thereon by mechanical means. In the case of closed subgingival systems, by contrast, the implant is embedded as far as the level of the alveolar crest, and the mucoperiosteal cover is sewn over the implant. Once the implant has become incorporated, a second operation is needed to be able to apply the abutment and the desired bridge, crown or other prosthesis thereon. A disadvantage of all systems in which the prosthesis is adhesively bonded onto the abutment is that it is difficult to remove the residues of adhesive or of cement that emerge in the transition area between crown and abutment and/or implant during adhesive bonding.

A two-part, open transgingival system is offered by Institut-Straumann AG, Waldenburg, Switzerland, under the name ITI DENTAL IMPLANT SYSTEM. The anchoring part or implant, which is implanted through the gum, and also the associated attachment parts are in this case made of pure titanium. EP 0879024 B1 discloses a similar system in which a solid conical abutment is screwed into the implant. The receiving opening of the implant accordingly also has a conical shape. Such a conical shape is favoured by dentists since it simplifies the implantation, in particular also the taking of impressions and the production of master models. The conical connection between implant and abutment places high demands on the accuracy of fit of the structural parts, since said connection involves both a force fit and also a form fit. Such cone connections can at present be achieved with acceptable failure rates only in titanium implants having sufficiently congruent cone surfaces.

Since the dental implants have to take up considerable alternating loads during mastication, even the very slightest micromobility between the screwed structural parts leads to abrasion and wear.

It is known that the two-part systems composed of implant and abutment permit good adaptation to the geometric conditions arising in different indications. However, since the large number of components involved is regarded in principle as being disadvantageous in respect of the mechanical stability of the overall system, and since every further connection represents a possible site of attack for periodontitis or gingivitis through cleft formation, document DE 10159683, also from Straumann, proposes a one-part dental implant made of a zirconium oxide ceramic, as is known from U.S. Pat. No. 6,165,925. The implant for anchoring in the bone and the abutment for receiving a crown or bridge to be applied are made of a material based on zirconium oxide, in which case good osseointegration is achieved by special treatment of the surface with a maximum depth of roughness in the range of between 4 and 20 µm in the area of the anchoring part. The one-part implant body with integrally formed abutment has an anchoring part with a threaded portion and with a rounded lower end for screwing into the jaw bone. In a preferred embodiment, the upper end of the anchoring part merges via a slightly outwardly conically widened portion into an structural part that is formed integrally therewith and that extends in the continuation of the longitudinal axis of the threaded portion. The structural part has a frustoconical or conical shape and is provided with a flattening on one side. On the side directed towards the flattening, an axially extending groove formed in the outer surface extends downwards from the upper end face of the structural part and ends in a conical portion, which forms the attachment to the cone portion of the anchoring part. The flattening, in conjunction with the groove lying opposite it, serves for the form-fit engagement of a screwing tool, which has a correspondingly adapted socket. A disadvantage of this system is that at least the abutment has to be reworked after insertion into the mouth of the patient.

WO 2006/084346 A1 from Medin Tech discloses an implant system with an abutment made of a non-metallic material, which system comprises an implant and a prosthesis support, which in turn comprises an abutment and a collar element. Important features of the implant system are that the parts of the implant system are pushed linearly into one another and adhesively bonded to one another. Between a substantially cylindrical base post and a head part, the abutment has a cylindrical neck part with a lower projection which is designed as a polygon and serves for the radial positioning of the abutment in a corresponding recess in the shoulder of the implant. Triangular, pentagonal or heptagonal projections are described as being preferred and interact with corresponding triangular, pentagonal or heptagonal recesses in the implant shoulder and permit positioning of the abutment in three, five or seven different radial angle positions about the longitudinal axis of the implant. The central bore in the implant for receiving the base post is provided with an inner thread, which allows a screw cap or a spacer to be screwed in during the healing process. After the healing process, a collar element is pushed over the neck area of the abutment, and the base post is adhesively bonded into the threaded bore of the implant. The collar element arranged between implant and abutment must take up a considerable share of the mastication forces and, with its convex outer face, represents the surface of contact with respect to the surrounding gum. A central and continuous axial channel is arranged in the abutment to allow the adhesive to flow off. WO 2006/084346 A1 lists a whole series of ceramic and composite materials that are suitable for production of the abutment. A disadvantage of this system lies in the considerable technical effort involved in producing the central axial channel in the abutment and also in the mechanical loads and stresses to which the abutment is thereby exposed. The abutment, or the positioning element of the abutment, must therefore either be made of a material that withstands high mechanical stresses or, as has been mentioned above, must be suitably dimensioned. A further disadvantage is that the implant cannot be produced from ceramic material, with the result that a purely ceramic system composed of ceramic implant and ceramic abutment cannot be achieved according to the invention in WO 2006/084346 A1.

EP 1728486 A1 from Straumann discloses an implant system with an implant and an abutment, in which the abutment is provided with means for rotationally locked mounting of the abutment in the implant. A receiving opening in the implant is designed in such a way that a base portion of the abutment can be inserted substantially with a form fit and at the desired angle position into the receiving opening of the implant and is secured in this position on the implant by a separate screw. To receive the screw, the abutment is provided with a central continuous bore, such that the base area has to be designed with a very thin wall. The means that prevent twisting of the abutment and implant relative to each other consist in turn of a polygonal anti-rotation element on the abutment and of a recess that has a shape corresponding to the anti-rotation element. The system in EP 1728486 A1 does not allow the implant and abutment to be produced from ceramic at reasonable cost using known production methods and techniques.

Despite the large number of known systems for replacing individual teeth, for treating large gaps between the teeth and shortened rows of teeth and for securing bridges or prostheses, there is an increasing need among users for systems that avoid the disadvantages of the known systems.

SUMMARY OF THE INVENTION

It is an object of the invention to make available a generic tooth replacement system that does not have the abovementioned disadvantages. A further object is to make available a tooth replacement system comprising an implant and an abutment, which system ensures an optimized introduction of force from the abutment into the implant. In addition, the tooth replacement systems according to the invention are intended to permit complete freedom of choice of material in the production and combination of abutments and implants made of metal and/or ceramic. They are to be simple and inexpensive, and the tooth replacement system is intended to meet the very highest demands in respect of stability, quality and useful life.

This object is achieved by a tooth replacement system comprising an implant for osseointegration in a jaw bone and an abutment, wherein an abutment stem comprising a close-fit cylinder can be fitted in a corresponding cylindrical close-fit seat of a receiving opening in the implant.

An important advantage of the present invention is that the latter can be implemented in virtually all tooth replacement systems in which the crown, bridge or other prosthesis is adhesively bonded or cemented to implant and/or abutment. In the text below, the word crown, unless expressly stated otherwise, is also intended to mean bridges and all other forms of prostheses. The term adhesive bonding, unless expressly stated otherwise, is intended to include all known cohesive joining methods, that is to say methods in which an adhesive connection is to be made between the structural groups that are to be connected, and, accordingly, the term adhesive is intended to include all compositions known for cohesive joining in dentistry.

In the tooth replacement systems according to the invention, the transmission of all the forces acting between abutment and implant is limited to two clearly defined areas. These two areas are preferably a cylindrical area of axial extent on a proximal abutment stem, which can be fitted into a corresponding cylindrical receiving opening in the implant, and a base surface which is preferably arranged perpendicular to the longitudinal axis at the proximal end of the abutment and which, when the abutment is inserted, bears on the bottom surface in the receiving opening. While the cylindrical operative connection primarily takes up the shearing forces, the plane operative connection primarily takes up the axial forces. The relatively simple geometry of the fits makes it easier to maintain very small tolerances during production, particularly also in the ceramic area.

It has proven advantageous to design implant and abutment in such a way that, when the abutment is inserted, the head area of the abutment is spaced apart from a distal shoulder surface of the implant, such that the force transmission is clearly limited to the two aforementioned areas.

In the tooth replacement systems according to the invention, the abutment is preferably adhesively bonded in the receiving opening. So as to avoid having to weaken the abutment with a central outflow bore, as is known from the prior art, the cylindrical abutment stem in preferred embodiments is provided with at least one peripheral drainage channel for drainage of adhesive. The at least one drainage channel extends along the entire height of the cylindrical abutment stem and, in further embodiments, can be supplemented or replaced by a matching channel in the cylindrical inner wall of the implant.

Another advantage of the present invention is that it can be implemented not only in conventional implants, but also in implants that are constructed in accordance with the concept of platform switching. In the latter, preservation of the crestal bone is attempted by targeted combination of a smaller abutment diameter and a greater implant platform.

In preferred embodiments of the tooth replacement systems according to the invention, the form-fit interaction of locking means on abutment and implant achieves a reliable positioning with subsequent blocking of the abutment in a plurality of predefined discrete angle positions. The torque-positive connection in the area of the proximal abutment base and of at least one inner wall of a proximal portion of the receiving opening ensures that the implant according to preferred embodiments can be positioned in at least two discrete radial angle positions.

Without departing from the basic idea of the present invention, such tooth replacement systems in which abutment and/or implant do not have any locking means can also be realized such that the abutment can be rotated about the longitudinal axis and is not rotationally locked, even in the assembled state.

BRIEF DESCRIPTION OF THE FIGURES

The invention is explained below with reference to the figures, which merely depict illustrative embodiments and in which:

FIG. 3b shows the abutment according to FIG. 3a in an oblique view from the proximal direction;

FIG. 4b shows the abutment according to FIG. 4a in an oblique view from the proximal direction;

FIG. 5b shows the abutment according to FIG. 5a in an oblique view from the proximal direction.

DETAILED DESCRIPTION OF PREFERRED EMBODIMENTS

Figure 1:
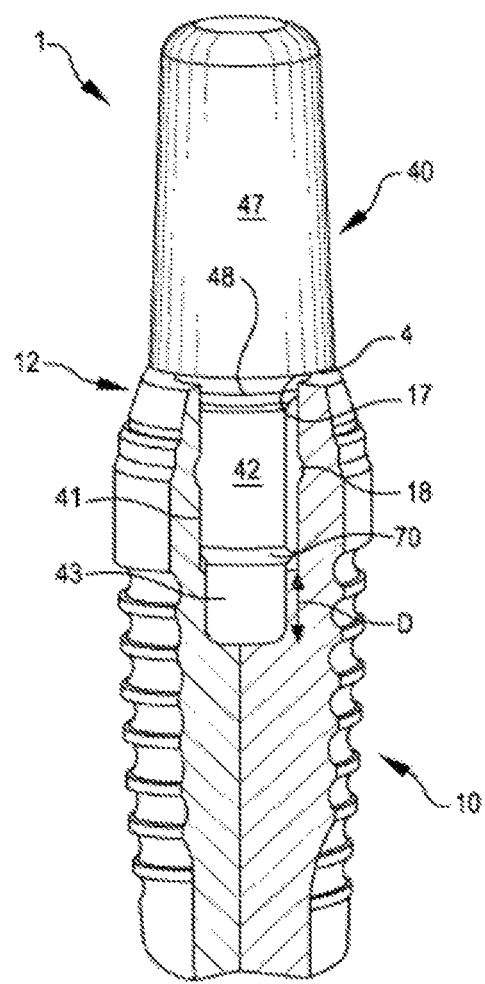
FIG. 1 shows an implant of a tooth replacement system according to a first embodiment of the invention in a sectorial longitudinal section along the central axis, with an abutment inserted and with the crown omitted.
Figure 2:
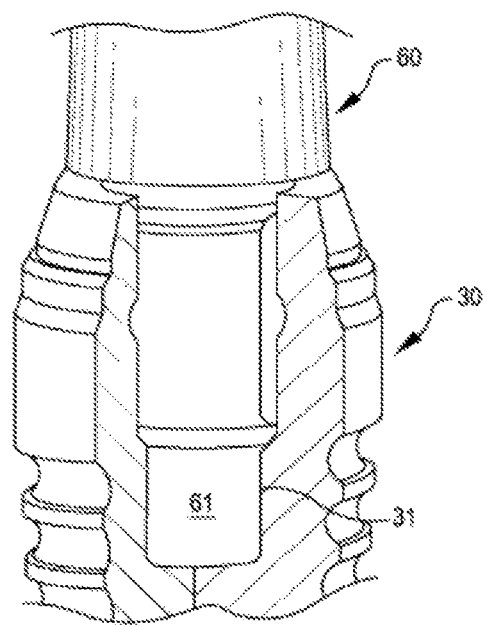
FIG. 2 shows a detailed enlargement of a further tooth replacement system according to the invention in a sectorial longitudinal section along the central axis in the area of the operative connection between inserted abutment and implant.

FIG. 1 shows a tooth replacement system 1 with a partially sectioned implant 10, so as to provide a free view of an abutment 40 with a cylindrical abutment stem 41 that is fitted in a corresponding cylindrical receiving opening 11 in the implant 10. The abutment stem 41 has a cylindrical outer jacket surface, or close-fit cylinder 42, which is produced with a shape exactly matching the cylindrical receiving opening 11 with a play of at most 30 µm, preferably 10 µm with a tolerance of +/−5 µm. The abutment stem 41 narrows in a proximal area 43 which, in the illustrative embodiment depicted, is provided with an external hexagon 44. The function of the external hexagon 44 as a locking means for securing against twisting or blocking against rotation is discussed in greater detail below.

In all of the illustrative embodiments shown, the coronal end 12 of the implant 10 is provided with the receiving opening 11 in the form of a cylindrical blind bore, which opens out coaxially at the lower end in an internal hexagon 13, in order to receive the abutment 40. In the assembled state shown, the corresponding external hexagon 44 of the abutment engages in the internal hexagon 13 so as to secure against twisting.

The abutment 40 is preferably adhesively bonded into the implant 10, such that a force-fit and form-fit connection is produced between the close-fit cylinder 42 of the abutment stem 41 and the corresponding cylindrical close-fit seat 14 provided in the receiving opening in the implant. The cylindrical implant/abutment connection, which is very advantageously able to take up shearing forces, is supplemented by a proximal bottom surface 45 of the abutment stem 41 bearing with a force fit on the bottom 15 of the internal hexagon 13 and thus of the receiving opening 11, which limits the axial movement of the abutment downwards. In the assembled state, the axial forces acting on the abutment 40 are primarily introduced into the implant 10 via this force-fit bearing.

The coronal end 12 of the implant 10 is formed by a distal annular surface 16 that extends approximately horizontally to the central axis and that surrounds the receiving opening 11. When the abutment 40 is inserted, an annular gap 4 is formed between the distal annular surface 16 and a proximal flange 46 provided in the transition area between the abutment stem 41 and the head area 47 of the abutment 40. This prevents the head area 47 of the abutment 40 from coming to lie on the distal annular surface 16 of the implant 10 and ensures that force is introduced from the abutment 40 into the implant 10 only by way of the close-fit cylinder 42 in the stem area 41 and the base surface 45.

Figure 3A:
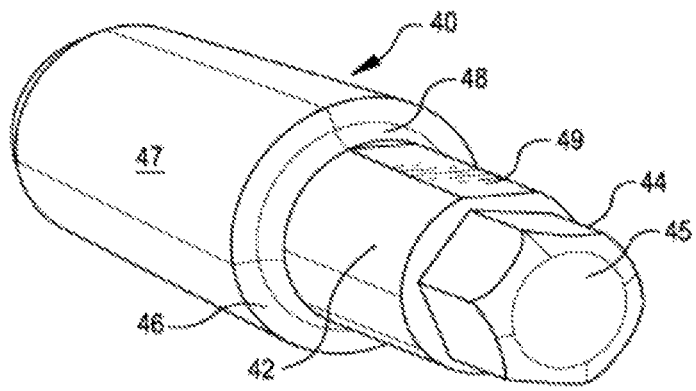
FIG. 3a shows a side view of an abutment according to FIG. 1, which abutment has been turned 60° clockwise relative to the view in FIG. 1.

From FIG. 3A which shows the abutment 40 according to FIG. 1 turned through approximately 60°, it will be evident that a slightly indented neck area 48 is provided between the substantially cylindrical abutment stem 41 and the head 47 of the abutment 40. When the abutment 40 is inserted, an inner edge 17 between the distal annular surface 16 and the cylindrical close-fit seat 14 comes to lay exactly level with the circumferential constriction in the neck area 48, such that the edge 17 is free relative to the abutment 40 and is protected even when the abutment 40 is loaded.

The axial dimensions of the individual interacting portions 14 and 42, 15 and 45 of the abutment 40 and of the implant 10 are adapted to each other in such a way that, with the abutment inserted fully, the annular gap 4 between abutment head 47 and distal annular surface 16 of the implant is at least 10 µm, preferably between 10 and 50 µm, particularly preferably 20 µm. As can be seen from FIG. 1, the height Hv of the means of securing against twisting, or external hexagon, is greater than the depth D of the corresponding internal hexagon 13 in the implant, such that the proximal end area 70 of close-fit cylinder 42 on the abutment stem 41 is safely offset relative to the internal hexagon 13 and there can be no undesired contact and loading here with axial force components.

Figure 3C:
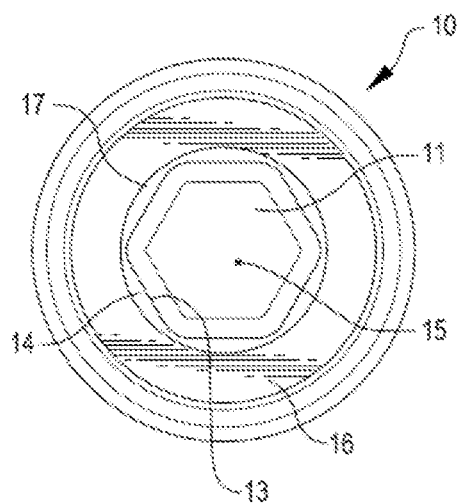
FIG. 3c shows the implant according to FIG. 1 in a view from the distal direction into the receiving opening.

It is also clear from the views in FIGS. 3A and 3B 3A-3C that, at least in the area of the cylindrical implant/abutment connection 14, 42, the cylindrical abutment stem has at least one drainage channel 49, which extends axially on the outside along the entire height of the close-fit cylinder 42. When the abutment 40 is adhesively bonded into the implant 10, the at least one drainage channel 49 ensures unimpeded removal of the excess adhesive from the receiving opening 11. In the illustrative embodiment shown, the drainage channel is formed by a simple tangential flattening of the close-fit cylinder 42. Upon axial insertion of the abutment into the adhesive-filled receiving opening, the interaction between the drainage channel and the adjacent inner wall of the close-fit seat 14 results in the formation of the functional outflow channel with the cross section in the shape of a sector of a circle. The at least one drainage channel is between 10 μm and 250 μm deep, preferably between 50 and 150 μm deep, giving a functional cross-sectional surface area of the drainage channel of preferably between 1 and 10%, preferably of 2%, relative to the cross-sectional surface area of the abutment stem. It will be evident to a person skilled in the art that the dimensions of the drainage channel do not have to be limited to these preferred values, and instead can be optimized in conjunction with various factors such as the dimension of the abutment, the choice of material, stability and others.

The simple and at the same time effective design of the drainage channel makes it possible to dispense with central channels in the inside of the abutment, a fact that has a positive effect on stability and also on the production work and production costs.

FIG. 1 shows a circumferential annular groove 18 in the cylindrical close-fit seat 14 of the receiving opening 11, which annular groove 18 has proven extremely advantageous, for example, for the releasable clamping of plastic incorporation caps.

Figure 4A:
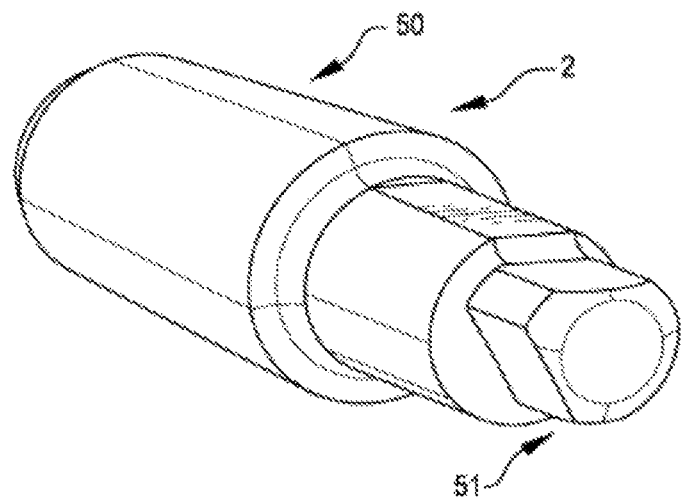
FIG. 4a shows a side view of an abutment according to a further embodiment of the invention.
Figure 5A:
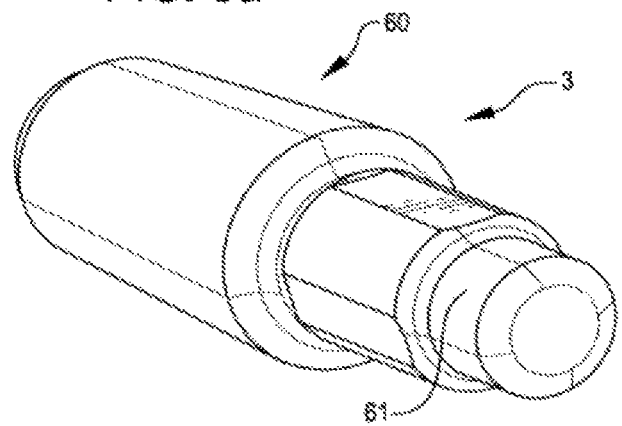
FIG. 5a shows a side view of an abutment according to FIG. 2, which abutment has been turned 60° clockwise relative to the view in FIG. 2.
Figure 4C:
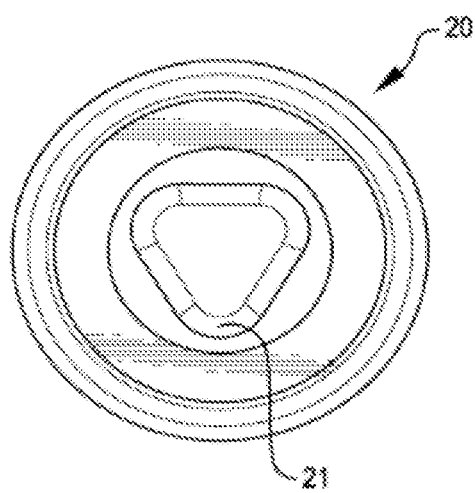
FIG. 4c shows an implant suitable for receiving the abutment according to FIG. 4a and FIG. 4b, in a view from the distal direction into the receiving opening.
Figure 5C:
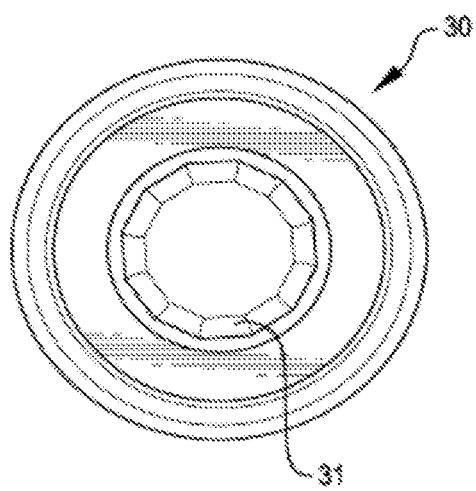
FIG. 5c shows the implant according to FIG. 2 in a view from the distal direction into the receiving opening.

With reference to the illustrative embodiment in FIGS. 4A-C, another advantageous embodiment will be discussed in which the inserted abutment 50 is blocked securely against twisting in the implant 20 by the form-fit interaction of locking means 21, 51 which have a cross section substantially in the shape of an equilateral triangle.

In the embodiment in FIGS. 2 and 5A-C, an abutment 60 is shown that has no locking means at the proximal abutment base 61 and instead has a circular cylindrical shape. The abutment 60 is therefore freely rotatable in a receiving opening with a twelve-sided proximal portion 31 in the implant 30.

The tooth replacement systems according to the invention can preferably be positioned in at least two radial angle positions. The polygonal locking means in the proximal area of the receiving openings of the implants serve, on the one hand, as aids for the radial positioning and rotationally locked mounting of the abutment in the implant and for receiving the screwing tool in a torque-positive manner when the implant is being screwed in. The location directly above the solid, externally threaded proximal part of the implant permits optimal force transmission, with minimal torsional loading of thin-walled implant areas during insertion into the jaw bone.

From the present disclosure, it will be readily apparent to a person skilled in the art that the tooth replacement systems according to the invention permit maximum freedom of choice of material. The implants and also the abutments can be made from titanium or ceramic, and both structural parts can be used in all possible material combinations. This permits for the first time the insertion or adhesive bonding of ceramic abutments into implants made from titanium oxide or other metallic materials.

The advantages, however, are most evident in the production of implants and abutments made from ceramics. Ceramic production materials that have proven particularly useful are known zirconium oxide or zirconium oxide/aluminium mixtures.

Although only axially symmetrical abutments are depicted in the illustrative embodiments, the teaching according to the invention can also be applied to abutments having a head that is angled with respect to the stem. The same is true of the slightly conical shape of the abutment head, which can easily also be designed, preferably in the case of ceramic abutments, as a cylinder for individual reshaping.

In contrast to previously known abutments that are screwed into the implant, the connection according to the invention between implant and abutment avoids the risk of stresses occurring in the system and/or of screw fractures being caused by overloading.

| LIST OF REFERENCE NUMBERS | |
| --- | --- |
| tooth replacement system | 1, 2, 3 |
| annular gap | 4 |
| implant | 10, 20, 30 |
| receiving opening | 11, 21, 31 |
| coronal end | 12 |
| internal hexagon | 13 |
| close-fit seat | 14 |
| bottom | 15 |
| annular surface | 16 |
| inner edge | 17 |
| annular groove | 18 |
| abutment | 40, 50, 60 |
| abutment stem | 41, 51, 61 |
| close-fit cylinder | 42 |
| narrowing | 43 |
| external hexagon | 44 |
| bottom surface | 45 |
| flange | 46 |
| head | 47 |
| neck | 48 |
| drainage channel | 49 |

The invention claimed is:

1. A tooth replacement system comprising an implant for osseointegration in a jaw bone and an abutment comprising a head area and an abutment stem, wherein the implant comprises a receiving opening that terminates at a bottom surface, the abutment extends from a distal surface to a proximal bottom surface of the abutment stem and the abutment stem comprises:
   (a) a close-fit cylinder fitted in a corresponding cylindrical close-fit seat of the receiving opening;
   (b) a proximal abutment base positioned at a proximal end of the close-fit cylinder and having a reduced diameter relative to the close-fit cylinder that is received in a reduced diameter area of the receiving opening; and
   (c) a circular constriction in an indented neck area between the abutment head area and the close-fit cylinder,
   wherein, when the abutment is inserted, the proximal bottom surface of the abutment stem bears on the bottom surface of the receiving opening and wherein the proximal abutment base has a height that is greater than a depth of the reduced diameter area of the receiving opening, whereby an inner edge between a distal annular surface of the implant and the close-fit seat is level with the circumferential constriction of the abutment such that the inner edge and the distal annular surface are free of the abutment head area.

2. A tooth replacement system according to claim 1, wherein the abutment can be adhesively bonded in the receiving opening.

3. A tooth replacement system according to claim 2, wherein the abutment stem is provided with a peripheral drainage channel for drainage of adhesive when the abutment is adhesively bonded into the implant.

4. A tooth replacement system according to claim 3, wherein the peripheral drainage channel is formed by a flattening of the abutment stem.

5. A tooth replacement system according to claim 4, wherein the peripheral drainage channel has a cross section shaped as a sector of a circle and is between 10 μm and 250 μm deep.

6. A tooth replacement system according to claim 5, wherein the peripheral drainage channel is between 50 μm and 150 μm deep.

7. A tooth replacement system according to claim 6, wherein the implant and/or abutment are made from titanium or ceramic.

8. A tooth replacement system according to claim 1, wherein the implant and/or abutment are made from titanium or ceramic.

9. A tooth replacement system according to claim 1, wherein the implant and/or the abutment are made from zirconium oxide or a zirconium oxide/aluminum mixture.

10. A tooth replacement system according to claim 1, wherein the abutment can be positioned in at least two radial angle positions by form-fit interaction of locking means on the proximal abutment base with a proximal portion of the receiving opening.

11. A tooth replacement system comprising an implant for osseointegration in a jaw bone and an abutment comprising an abutment head and an abutment stem, wherein the implant comprises a receiving opening that terminates at a bottom surface, the abutment extends from a distal surface to a proximal bottom surface of the abutment stem and the abutment stem comprises:
   (a) a close-fit cylinder fitted in a corresponding cylindrical close-fit seat of the receiving opening; and
   (b) a proximal abutment base positioned at a proximal end of the close-fit cylinder and having a reduced diameter relative to the close-fit cylinder that is received in a reduced diameter area of the receiving opening; and
   (c) a circular constriction in an indented neck area between the abutment head and the close-fit cylinder, wherein, when the abutment is inserted, the proximal bottom surface of the abutment stem bears on the bottom surface of the receiving opening and wherein the proximal abutment base has a height that is greater than a depth of the reduced diameter area of the receiving opening, whereby, when the abutment is inserted in the implant, an inner edge between a distal annular surface of the implant and the close-fit seat is level with the circumferential constriction of the abutment such that the inner edge and the distal annular surface are free of the abutment head.

12. A tooth replacement system according to claim 11, wherein the abutment can be adhesively bonded in the receiving opening.

13. A tooth replacement system according to claim 11, wherein the abutment stem is provided with a peripheral drainage channel for drainage of adhesive when the abutment is adhesively bonded into the implant.

14. A tooth replacement system according to claim 13, wherein the peripheral drainage channel is formed by a flattening of the abutment stem.

15. A tooth replacement system according to claim 13, wherein the peripheral drainage channel has a cross section shaped as a sector of a circle and is between 10 μm and 250 μm deep.

16. A tooth replacement system according to claim 13, wherein the peripheral drainage channel is between 50 μm and 150 μm deep.

17. A tooth replacement system according to claim 11, wherein the implant and/or the abutment are made from zirconium oxide or a zirconium oxide/aluminum mixture.

18. A tooth replacement system according to claim 11, wherein the abutment can be positioned in at least two radial angle positions by form-fit interaction of locking means on the proximal base region with a proximal portion of the receiving opening.

19. A tooth replacement system according to claim 11, wherein an annular gap of at least 10 μm is formed between the abutment head and a distal annular surface of the implant.

20. A tooth replacement system according to claim 19, wherein the annular gap is between 10 μm and 50 μm.

21. A tooth replacement system according to claim 19, wherein the annular gap is 20 μm.

* * * * *